(12) United States Patent
Kocal et al.

(10) Patent No.: US 6,555,715 B1
(45) Date of Patent: Apr. 29, 2003

(54) CONVERSION OF LIGHT PARAFFINS TO OXYGENATES OR OLEFINS USING AN IMIDE PROMOTER

(75) Inventors: Joseph A. Kocal, Glenview, IL (US); Robert R. Frame, Glenview, IL (US); Jeffery C. Bricker, Buffalo Grove, IL (US)

(73) Assignee: UOP LLC, Des Plaines, IL (US)

( * ) Notice: Subject to any disclaimer, the term of this patent is extended or adjusted under 35 U.S.C. 154(b) by 131 days.

(21) Appl. No.: 09/975,371

(22) Filed: Oct. 11, 2001

(51) Int. Cl.⁷ ............................................... C07C 45/28
(52) U.S. Cl. .................. 568/383; 568/399; 568/881; 568/884; 568/885; 568/910; 568/470; 502/155; 502/162; 502/166; 585/639; 585/640; 585/649
(58) Field of Search ................................. 502/155, 162, 502/166; 568/881, 884, 885, 383, 399, 470, 910; 585/649, 639, 640

(56) References Cited

U.S. PATENT DOCUMENTS

| | | | |
|---|---|---|---|
| 4,131,741 A | * | 12/1978 | Bartlett et al. |
| 4,795,730 A | * | 1/1989 | Drake et al. |
| 5,395,980 A | | 3/1995 | Mueller et al. ............. 568/573 |
| 5,684,215 A | * | 11/1997 | Horn et al. |
| 5,958,821 A | | 9/1999 | Ishii et al. ................... 502/167 |

OTHER PUBLICATIONS

Shun–Ichi Murahashi et al., *J. Chem. Commun.*, 139–140, (1993).
*Catalysis Letters* 8, 45–52 (1991).
*Tetrahedron Letters*, vol. 34, No. 8 1299–1302 (1993).
G.P. Khrnova et al., *Petrol Chem. U.S.S.R.*, vol. 21, No. 1, 49–52 (1981).
Y. Ishii et al., *Catalysis Surveys*, 27–35 (1999).
Y. Ishii et al., *J. Org. Chem.*, vol. 61, 4520–4526 (1996).

* cited by examiner

*Primary Examiner*—Shailendra Kumar
(74) *Attorney, Agent, or Firm*—John G. Tolomei; Frank S. Molinaro

(57) ABSTRACT

A process has been developed for oxygenating linear $C_2$ to $C_6$ alkanes to ketones or aldehydes. The process involves reacting the alkanes with oxygen in the presence of a catalyst comprising an imide promoter and a metal co-catalyst. An example of the imide is N-hydroxyphthalimide and an example of the co-catalyst is Co (acetylacetonate). The process is preferably carried out using an inert solvent, an example of which is acetic acid. Optionally, the oxygenated product can be hydrogenated to give the corresponding alcohol which can optionally in turn be dehydrated to provide the corresponding olefin.

25 Claims, No Drawings

CONVERSION OF LIGHT PARAFFINS TO OXYGENATES OR OLEFINS USING AN IMIDE PROMOTER

FIELD OF THE INVENTION

This invention relates to a process for reacting $C_2$ to $C_6$ alkanes with oxygen in the presence of a catalyst comprising an imide promoter and a metal co-catalyst to provide an oxygenated product. The oxygenated product can be further reacted with hydrogen to form the corresponding alcohol and the alcohol can be dehydrated to provide the corresponding olefin.

BACKGROUND OF THE INVENTION

Organic compounds containing an oxygen in the structure have various industrial uses either in and of themselves or as precursors to more valuable materials. These oxygenated organic compounds are usually prepared by processes which convert hydrocarbons to the oxygen containing organic compounds. Although saturated hydrocarbons such as paraffins and naphthenes are the lowest cost and most readily available hydrocarbons, they are also very stable and thus not very chemically reactive. In particular, linear paraffinic compounds are the hardest to oxygenate. It would be very desirable to easily convert paraffins (and especially linear paraffins) to oxygenates.

There are a number of reports in the literature of various ways to oxidize hydrocarbons to the corresponding aldehyde or ketone. One reference is U.S. Pat. No. 5,958,821 B1 which discloses oxidizing various hydrocarbons such as cycloalkanes, aromatic hydrocarbons, etc. with oxygen in the presence of an oxidation catalyst comprising an imide compounds such N-hydroxyphthalimide and a metal compound co-catalyst such as cobalt or manganese acetyl acetonate. The patentee of the '821 reference enumerates virtually every class of known hydrocarbons and virtually every metal in the periodic table. Other references which have addressed the oxygenation of alkanes include Shun-Ichi Murahashi et al. in *J. Chem. Soc., Chem. Commun.*, 139–140 (1993) in which the authors present results for the oxidation of alkanes and alkenes with oxygen in the presence of aldehydes and using a copper compound catalyst. Their results showed that linear alkanes such as N-decane had extremely low conversion. In *Catalysis Letters* 8 (1991), 45–52 the same authors have shown that isobutane can react with oxygen in the presence of an iron perhaloporphyrin complex to give mostly tert-butyl alcohol. Shun-Ichi Murahashi et al. have reported in *Tetrahedron Letters*, vol. 34, no. 8 pp. 1299–1302, 1993 the ruthinium catalyzed oxidation of alkanes with alkyl hydroperoxide. Specifically, they reacted n-heptane and n-decane to provide ketones and alcohols., G. P. Khirnova et al. in *Petrol. Chem. U.S.R.R.* vol. 21, no. 1, pp. 49–52, 1981 have reported the liquid phase oxidation of isobutane using a heterogeneous catalyst containing cobalt and molybdenum borides or molybdenum carbides. The main products of this reaction were tert-butyl hydroperoxides, tert-butyl alcohol and acetone. It has also been shown in U.S Pat. No. 5,395,980 B1 that isobutane can be converted to tert-butyl hydroperoxide at elevated temperatures (about 140° C.) by reacting it with oxygen in the presence of tert-butyl alcohol and di (tert-butyl) peroxide.

There are also reports of the oxidation of alkanes with oxygen using N-hydroxyphthalimide (NHPI) as a catalyst and a metal compound co-catalyst. For example, Y. Ishii et al. in Catalysis Surveys *from Japan* 3 (1999 27–35) report the oxidation of various alkanes including isobutane. The isobutane gave tert-butyl alcohol and acetone and tert-butyl hydroperoxide. The other alkanes which were tested were all branched alkanes. No results are presented for the oxidation of n-butane using NHPI as the catalyst. Ishii et al. in *J. Org. Chem.* 1996, 61, 4520–4526 present results of the oxidation of various cycloalkanes using NHPI and Co(acac)$_n$. Results are also presented for the oxidation n-octane to give octanols and octanones.

The above references show that branched alkanes can be oxidized using various catalytic systems, whereas light normal paraffins ($C_2$–$C_6$) require very strong oxidants such as hydrogen peroxide or organic peroxides. The references by Ishii et al. indicate that only branched low molecular weight alkanes, e.g. isobutane, and longer chain alkanes e.g. octane, can be converted to alcohols or ketones using NHPI and a metal co-catalyst.

Despite the reports in the literature as to the unreactivity of linear light paraffins, applicants have surprisingly found that $C_2$ to $C_6$ linear alkanes can be converted to ketones or alcohols using a catalyst comprising NHPI (and its derivatives) in combination with a metal co-catalyst. In particular, applicants have found that propane and n-butane can be converted to acetone and methyl ethyl ketone respectively at a selectivity of greater than 90% by reacting the alkanes with an 8% oxygen/nitrogen gas at 70° C. using a catalyst comprising NHPI and a cobalt (acac) co-catalyst in acetic acid.

SUMMARY OF THE INVENTION

As stated, this invention relates to a process for converting light paraffins to the corresponding oxygenated compounds and optionally then proceeding to convert the oxygenated compounds to the corresponding olefins. Accordingly, one embodiment of the invention is a process for converting light paraffins to an oxygenated compound, comprising reacting light paraffins selected from $C_2$ to $C_6$ linear alkanes, with oxygen, in the presence of a catalyst comprising at least one imide promoter and a co-catalyst at oxidation conditions to provide an oxygenated compound, the imide having the formula:

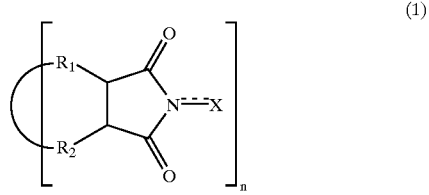

(1)

where $R_1$ and $R_2$ are independently selected from the group consisting of hydrogen, halogens, alkyl groups, cycloalkyl groups, aryl groups, hydroxyl group, alkoxy groups, carboxyl group, alkoxycarbonyl groups and acyl groups or $R_1$ and $R_2$ may bind to form a double bond, an aromatic ring or a non-aromatic ring; X is oxygen or a hydroxyl group and n=1 and the co-catalyst comprising at least one metal selected from the group consisting of Groups IVB, VB, VIB, VIIB, VIII elements of the Periodic Table of Elements to provide an oxygenated compound.

Another embodiment of the invention is to take the oxygenated compound of the previous paragraph and react it with hydrogen in the presence of a hydrogenation catalyst at hydrogenation conditions to provide alcohols and then optionally contacting the alcohols with a dehydration catalyst to provide olefins.

These and other objects and embodiments will become clearer after a detailed description of the invention.

DETAILED DESCRIPTION OF THE INVENTION

As stated the present invention relates to a process for converting light paraffins, i.e., alkanes to oxygenated compounds and optionally converting the oxygenated compounds to olefins. The light alkanes which are within the scope of the invention are the linear alkanes having from 2–6 carbon atoms, especially $C_2$ to $C_4$ linear alkanes and more particularly propane and n-butane. Although a feedstream comprising single alkane is preferred to be used in the present process, the feedstream to the process will usually contain a mixture of two or more alkanes, with one alkane being the major component. The process generally involves reacting the alkanes with oxygen in the presence of a catalyst comprising an imide promoter and a metal co-catalyst. Accordingly, one essential element of the catalyst of the present invention is an imide promoter. The imide promoter is represented by the general formula (1):

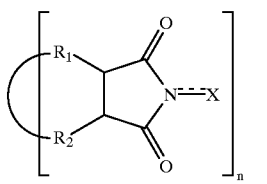

(1)

where $R_1$ and $R_2$ are independently selected from the group consisting of hydrogen, halogens, alkyl groups, cycloalkyl groups, aryl groups, hydroxyl group, alkoxy groups, carboxyl group, alkoxy-carbonyl groups and acyl groups or $R_1$ and $R_2$ may bind to form a double bond, an aromatic ring or a non-aromatic ring; X is oxygen or a hydroxyl group and n=1.

In the imide compound shown by formula 1, when $R_1$ and/or $R_2$ represent halogens, these include iodine, bromine, chlorine and fluorine. Alkyl groups include without limitations, methyl, ethyl, propyl, isopropyl, butyl, isobutyl, hexyl, heptyl, or other straight chains or branched chain alkyl groups having 1 to 10 carbon atoms, preferably 1 to 6 carbon atoms and most preferably 1 to 4 carbon atoms.

Specific examples of aryl or aromatic groups, without limitation, are phenyl groups and naphthyl groups. Cycloalkyl groups include without limitation cyclopentyl, cyclohexyl, cyclooctyl etc. Specific examples of alkoxy groups include methoxy, ethoxy, propoxy, butoxy, isobutoxy, isopropoxy and other alkoxy groups having from 1 to 10 carbon atoms, preferably 1 to 6 carbon atoms and most preferably 1 to 4 carbon atoms. Alkoxy-carbonyl groups include those having 1 to 10 carbon atoms, preferably 1 to 6 carbon atoms and most preferably 1 to 4 carbon atoms. Specific examples include, without limitation, methoxy carbonyl, ethoxy carbonyl, isopropoxy carbonyl, pentyl oxycarbonxyl, etc. Acyl groups are any of those containing 1 to 6 carbon atoms and include formyl, acetyl, propionyl, isobutyryl, etc.

When $R_1$ and $R_2$ bind to form a ring, the ring can be either aromatic or non-aromatic having from 5 to 12 carbon atoms and especially from 6 to 10 carbon atoms. Specific examples include but are not limited to cyclohexane, cyclohexene, benzene, naphthalene, 5-norbornene, etc. These rings additionally may be substituted with various moieties. Specific preferred imide compounds include those having the following formulas:

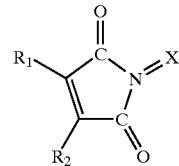

1(a)

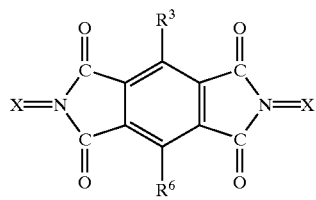

1(b)

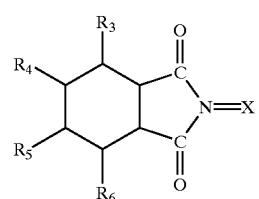

1(c)

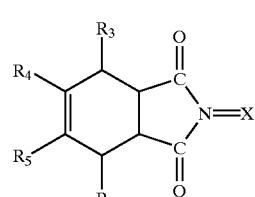

1(d)

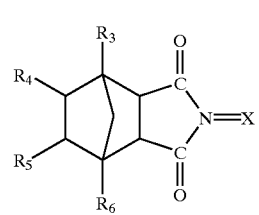

1(e)

where $R_3$, $R_4$, $R_5$ and $R_6$ represent the same or different moiety selected from the group consisting of hydrogen, an alkyl group, a hydroxyl group, an alkoxy group, a carboxyl group, an alkoxy-carbonyl group, an acyl group, a nitro group, a cyano group, an amino group and a halogen.

The alkyl groups particularly include those having from 1 to 6 carbon atoms. The alkoxy, alkoxy-carbonyl, acyl groups possible are any of the ones enumerated above for formula "1". Since X in the above formulas denotes an oxygen atom or hydroxy group, the bond between the nitrogen atom and X is either a single bond or a double bond and thus is shown as a single bond with a dashed-bond.

Specific examples of preferred imide compounds include N-hydroxy succinimide, hydroxy maleimide, hydroxyhexahydrophthalimide, N'-dihydroxycyclohexanetetracaboximide, N-hydroxyphthalimide, and N-hydroxytetrabromophthalimide, etc. An especially preferred imide compound is N-hydroxylphthalamide with the acronym NHPI. These imide compounds can be prepared by conventional methods in which an acid anhydride reacts with a hydroxylamine to give an imide. Some of these imides are commercially available.

Another essential element of the catalyst of this invention is a co-catalyst comprising a metal. The metals which can be used as the co-catalyst are any of the elements from groups IVB, VB, VIB, VIIB and VIII of the Periodic Table of the Elements (IUPAC 4 to 10) and preferably group VIII (IUPAC 8 to 10). The two nomenclatures for the Periodic Table are those set forth in the Periodic Table printed by the Los Alamos National Laboratory and available on the Internet at the URL http://pearl1.lanl.gov/periodic/. Preferred elements include without limitation Co, Mn, Ti, V, Zr, Cr, Mo, W, Re, Ru, Rh, Mg, Cu and mixtures thereof. These metals can be used homogeneously or heterogeneously. When used homogeneously, the metals are present as salts or chelated compounds. Non-limiting examples of salts are acetates, nitrates, carbonates and halides. Non-limiting examples of chelates which can form complexes with the metals are acetylacetonate, porphyrins and phthalocyanines.

Heterogeneous systems involve depositing the desired metal onto a support which has a sufficient surface area to disperse the metal but which is not affected by the solvents, reactants or products, i.e. refractory. The surface area (as measured by the B.E.T. method) should be greater than $5m^2/g$ and preferably from about $10m^2/g$ to about $500m^2/g$. Non-limiting examples of these refractory supports are aluminas, silica, zeolites and clays. The desired metal is dispersed on the support by conventional methods such as impregnation, co-precipitation, spray drying, etc. A common method is to impregnate the support with a solution containing a metal salt or chelate, drying and calcining the impregnated support. The metal can be present on the support as the metal, i.e. zero valent state, the oxide or a compound.

The amount of imide and co-catalyst can vary widely but it usually varies from about 0.1 to about 20 mole % with respect to the alkane for the imide and from about 0.005 to about 0.015 mole % with respect to the alkane as the metal for the co-catalyst.

As stated the desired alkane(s) is reacted with oxygen in order to form oxygenated products. The oxygen can be pure oxygen or any source of oxygen such as air. The amount of oxygen which is needed to carry out the oxidation ranges from about 0.5 to about 100 moles per mole of alkane (0.5:1 to 100:1) and preferably from about 2 to about 50 moles per mole of alkane (2:1 to 50:1). It is desirable to have an excess amount of oxygen.

The oxidation process of the invention is preferably conducted in an inert organic solvent. Examples of these inert solvents include without limitation, acetic acid, propionic acid and other carboxylic acids. Other solvents include hydroxycarboxylic acids, nitriles such as acetonitrile, benzonitrile, amides such as acetamide, dimethylformamide (DMF), etc. Preferred solvents are acetic acid and other organic acids, acetonitrile, benzonitrile and other nitriles. Although it is preferred to carry out the instant process using an inert solvent, the process can be carried out using the alkane(s) as the solvent.

The oxidation conditions for carrying out the process of the invention can vary considerably. The temperature for example can vary from about 30° C. to about 300° C., preferably from about 50° C. to about 200° C. and most preferably from about 70° C. to about 150° C. Although the reaction can be carried out at atmospheric pressure it is preferred to carry out the process at super atmospheric pressures in the range of about 100 kPa to about 100 MPa, preferably from about 500 kPA to about 50 MPa. The process can be carried out in a batch mode, a semi-batch mode or continuous flow mode in the presence of oxygen or under a steady flow of oxygen. In a batch mode, the desired reactants are contacted for a sufficient time to obtain adequate conversion of the alkanes, which is usually from about 30 minutes to about 48 hours, preferably from about 1 to 36 hours and more preferably from about 2 to about 24 hours. In a continuous mode a stream comprising the alkanes can be up or downflowed over a bed of catalyst at a liquid hourly space velocity (LHSV) of about 0.1 to about 20 $hr^{-1}$ preferably about 0.2 to about 10 $hr^{-1}$ and most preferably from about 0.5 to about 5 $hr^{-1}$. The imide can be part of the feedstream or be on the catalyst bed. The oxygen or oxygen containing gas can be introduced at one injection point or at multiple injection points. After the desired contact time, the reaction product can be separated from the rest of the reaction mixture and purified according to conventional techniques such as filtration, condensation, distillation, extraction, crystallization, etc.

The oxygenated hydrocarbon can be used as is or it can optionally be reacted with a hydrogen containing gas in the presence of a hydrogenation catalyst to give the corresponding reduced oxygenated hydrocarbon. This can be carried out either before or after isolation of the reaction product. Again, the process can be carried out in a batch or continuous mode with continuous mode being preferred. Hydrogenation conditions include a temperature of about 20° C. to about 200° C., a pressure of about 340 kPa to about 28,000 kPa (50 to about 4,000 psig) and a liquid hourly space velocity of about 0.5 to about 10 $hr^{-1}$. In a batch mode the contact time varies from about 1 minute to about 5 hrs.

The hydrogenation catalyst comprises a hydrogenation component dispersed on a suitable support. Hydrogenation catalyst components include but are not limited to Group VIII metals of the Periodic Table, molybdenum, tungsten, nickel and mixtures thereof. Preferred hydrogenation components are the platinum group metals and nickel. The platinum group metals are platinum, palladium, rhodium, iridium, ruthenium and osmium. Preferred platinum group metals are platinum and palladium. The hydrogenation catalyst component is present in an amount from about 1 to about 10 wt. % as the metal. The support can be any support, which is inert to the reactants and products and has a sufficient surface area in order to disperse the hydrogenation component thereon. The surface area should be at least 5 $m^2/g$. Specific examples of supports include, but are not limited to, metal oxides, organic polymers, halogenated metal oxides, carbon and fluorinated carbon. These hydrogenation catalysts are prepared by conventional techniques in which one or more hydrogenation metal compounds are dissolved in a suitable solvent and then contacted with the support. Contacting can be done by impregnation, spray drying, etc. The final form of the hydrogenation component can be a metal, metal oxide or a metal compound.

The reduced oxygenated hydrocarbon can be further dehydrated to give the corresponding olefin. Dehydration processes are well known in the art and involve contacting the reduced oxygenate with a dehydration catalyst at dehydration conditions. Dehydration catalysts include liquid and solid acid catalysts. Non-limiting examples include sulfuric acid, solid phosphoric acid, aluminas, amorphous silica-alumina, heieropolyacids, sulfated zirconia and zeolites. Dehydration conditions include a temperature of about 50° to about 400° C. and preferably from about 100° to about 250° C., a liquid hourly space velocity (LHSV) of about 0.1 to about 1000 $hr^{-1}$ and a pressure of about 340 to about 28,000 kPa. The weaker the acid strength, the higher the temperature required.

The following examples are presented in illustration of this invention and are not intended as undue limitations on the generally broad scope of the invention as set forth in the appended claims.

EXAMPLE 1

A 600 cc autoclave was used to oxidize propane or n-butane. The autoclave contained acetic acid, propane (or n-butane), NHPI and Co (acetylacetonate) in a molar ratio of 40/10/1/0.1 respectively. The NHPI and Co (acetylacetanate) are commercially available. The autoclave was heated to various temperatures and held there for 5 hours. After cooling the contents were analyzed and the results presented in Table 1. It should be pointed out that it appeared that most of the reaction occurred in a much shorter time than five hours.

TABLE 1

Effect of Temperature on Alkane Oxidation

| Temp (° C.) | Alkane | Conversion (%) | Ketone* Select. (%) | Other Products (%)[1] |
|---|---|---|---|---|
| 70 | Propane | 3 | 100 | trace |
| 70 | n-butane | 10 | 85 | 15 |
| 135 | Propane | 17 | 98 | 2 |
| 150 | Propane | 33 | 97 | 3 |

*for propane the ketone observed was acetone for n-butane the ketone observed was methyl ethyl ketone (MEK)
[1]alcohol and corresponding ester The results in Table 1 show that the use of NHPI and a co-catalyst can preferentially oxidize light alkane to the corresponding ketone.

We claim as our invention:

1. A process for converting light paraffins to an oxygenated compound selected from the group consisting of ketones, aldehydes and alcohols comprising reacting at least one light paraffin selected from $C_2$ to $C_6$ linear alkanes, with oxygen, in the presence of a catalyst comprising an imide promoter and a co-catalyst at oxidation conditions to provide an oxygenated compound, the imide having the formula:

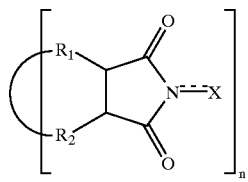

(1)

where $R_1$ and $R_2$ are independently selected from the group consisting of hydrogen, halogens, alkyl groups, cycloalkyl groups, aryl groups, hydroxyl group, alkoxy groups, carboxyl group, alkoxy-carbonyl groups and acyl groups or $R_1$ and $R_2$ may bind to form a double bond, an aromatic ring or a non-aromatic ring; X is oxygen or a hydroxyl group and n=1 and the co-catalyst comprising at least one metal selected from the group consisting of Groups IVB, VB, VIB, VIIB, VIII metals of the Periodic Table of Elements to provide an oxygenated compound.

2. The process of claim 1 where the imide compound is represented by any of the following formulae:

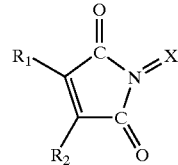
1(a)

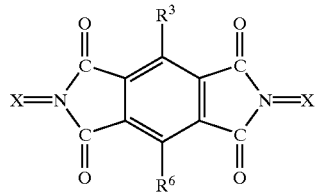
1(b)

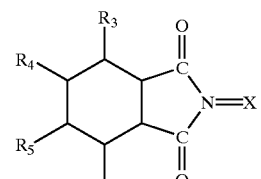
1(c)

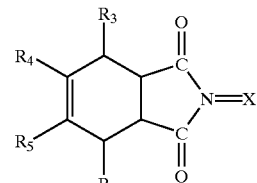
1(d)

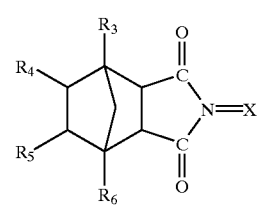
1(e)

where $R_3$, $R_4$, $R_5$ and $R_6$ represent the same or different moiety selected from the group consisting of hydrogen, an alkyl group, a hydroxyl group, an alkoxy group, a carboxyl group, an alkoxy-carbonyl group, an acyl group, a nitro group, a cyano group, an amino group and a halogen.

3. The process of claim 1 where the oxidation conditions comprise a temperature of about 30° C. to about 300° C., a pressure of about 100 kPa to about 100 MPa and a contact time sufficient to convert the alkanes to oxygenates.

4. The process of claim 3 where the process is carried out in a batch mode and the contact time varies from about 30 minutes to about 48 hours.

5. The process of claim 3 where the process is carried out in a continuous mode and at a liquid hourly space velocity of about 0.1 to about 20 $hr^{-1}$.

6. The process of claim 1 where the paraffin is at least one $C_2$ to $C_4$ linear alkane.

7. The process of claim 6 where the alkane is propane or n-butane.

8. The process of claim 1 where the metal is at least one metal from Group VIII of the Periodic Table of the Elements.

9. The process of claim 1 where the metal is selected from the group consisting of Co, Mn, Ti, V, Zr, Cr, Mo, W, Ru, Rh, Mg; Cu and mixtures thereof.

10. The process of claim 1 where the metal is present as a metal compound.

11. The process of claim 10 where the metal compound is a metal salt or a metal chelate.

12. The process of claim 11 where the salt is selected from the group consisting of acetate, nitrate, carbonate and halide.

13. The process of claim 11 where the chelate is selected from the group consisting of acetylacetonate, porphyrins and phthalocyanines.

14. The process of claim 1 where the imide is present in an amount of about 0.1 to about 20 mole % with respect to the alkane.

15. The process of claim 1 where the metal is present in an amount from about 0.005 to about 0.015 mole % as the metal with respect to the alkane.

16. The process of claim 1 where the process is carried out in a solvent selected from the group consisting of carboxylic acids, hydroxycarboxylic acids, nitrites, amides and mixtures thereof.

17. The process of claim 16 where the process is carried out in a solvent selected from the group consisting of acetic acid, propionic acid, acetonitrile, benzonitrile, acetamide, dimethylformamide and mixtures thereof.

18. The process of claim 1 where the oxygen is present in an amount of oxygen:alkanes of about 0.5:1 to 100:1.

19. The process of claim 1 further comprising reacting the oxygenated compound with hydrogen in the presence of a hydrogenation catalyst at hydrogenation conditions to provide an alcohol.

20. The process of claim 19 where the hydrogenation catalyst comprises a Group VIII metal, molybdenum, tungsten, nickel and mixtures thereof.

21. The process of claim 19 where the hydrogenation conditions comprise a temperature of about 20° C. to about 200° C., a pressure of about 340 kPa to about 28,000 kpa and a liquid hourly space velocity of about 0.5 to about 10 $hr^{-1}$.

22. The process of claim 19 further comprising, contacting the alcohol with a dehydration catalyst to provide an olefin.

23. The process of claim 22 where the dehydration catalyst comprises a liquid or solid acid.

24. The process of claim 23 where the dehydration catalyst is selected from the group consisting of sulfuric acid, solid phosphoric acid, aluminas, amorphous silica-alumina, heteropolyacids, sulfated zirconia and zeolites.

25. The process of claim 22 where the dehydration conditions comprise a temperature of about 50° C. to about 400° C., a LHSV of about 0.1 to about 1000 $hr^{-1}$ and a pressure of about 340 kPa to about 28,000 kPa.

* * * * *